United States Patent
Jones et al.

(10) Patent No.: US 8,226,689 B2
(45) Date of Patent: Jul. 24, 2012

(54) APPARATUS AND METHODS FOR SPINAL IMPLANT WITH VARIABLE LINK MECHANISM

(75) Inventors: Robert J. Jones, Austin, TX (US);
Charles R. Forton, Leander, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1171 days.

(21) Appl. No.: 11/234,706

(22) Filed: Sep. 23, 2005

(65) Prior Publication Data

US 2007/0083201 A1    Apr. 12, 2007

(51) Int. Cl.
*A61B 17/70*    (2006.01)

(52) U.S. Cl. ......... 606/250; 606/276; 606/277; 606/278

(58) Field of Classification Search ........... 606/246–279
See application file for complete search history.

(56) References Cited

U.S. PATENT DOCUMENTS

| | | | | |
|---|---|---|---|---|
| 5,312,402 A | * | 5/1994 | Schlapfer et al. | 606/53 |
| 5,312,405 A | | 5/1994 | Korotko et al. | |
| 5,474,551 A | * | 12/1995 | Finn et al. | 606/264 |
| 5,487,742 A | * | 1/1996 | Cotrel | 606/252 |
| 5,522,816 A | * | 6/1996 | Dinello et al. | 606/252 |
| 5,534,002 A | * | 7/1996 | Brumfield et al. | 606/278 |
| 5,569,246 A | | 10/1996 | Ojima et al. | |
| 5,624,442 A | | 4/1997 | Mellinger et al. | |
| 5,651,789 A | | 7/1997 | Cotrel | |
| 5,702,393 A | * | 12/1997 | Pfaifer | 606/328 |
| 5,743,911 A | * | 4/1998 | Cotrel | 606/250 |
| 5,947,966 A | | 9/1999 | Drewry et al. | |
| 5,980,523 A | | 11/1999 | Jackson | |
| 6,352,537 B1 | * | 3/2002 | Strnad | 606/276 |
| 6,368,320 B1 | * | 4/2002 | Le Couedic et al. | 606/61 |
| 6,554,832 B2 | | 4/2003 | Shluzas | |

(Continued)

FOREIGN PATENT DOCUMENTS

FR    2732887 A1    10/1996

(Continued)

OTHER PUBLICATIONS

International Search Report and Written Opinion for PCT/US2006/036429 mailed Dec. 28, 2006, 14 pages.

(Continued)

*Primary Examiner* — Eduardo C Robert
*Assistant Examiner* — Michelle C Eckman
(74) *Attorney, Agent, or Firm* — Seager Tufte & Wickem LLC

(57) ABSTRACT

A spinal implant provides support for desired parts of the spine. The implant can provide support in fusion situations. The spinal implant includes a pair of longitudinal rods and a transverse rod. A pair of variable cross-link devices couple the transverse rod, respectively, to the first and second longitudinal rods. Each variable cross-link device includes a body, having a curved member, a plug, and a rod engaging member. Fastening the plug into the body of the respective variable cross-link device causes application of force that couples the plug and the rod engaging member to the respective longitudinal rod. Fastening the plug also causes application of force that couples the rod engaging member to the transverse rod. Furthermore, fastening the plug causes application of force that couples the respective longitudinal rod to couple to the variable cross-link device. The surgical procedure may use minimally invasive surgery or non-minimally invasive surgery, as desired.

10 Claims, 8 Drawing Sheets

U.S. PATENT DOCUMENTS

| | | |
|---|---|---|
| 6,616,668 B2 | 9/2003 | Altarac et al. |
| 6,887,241 B1 | 5/2005 | McBride et al. |
| 7,250,052 B2 | 7/2007 | Landry et al. |
| 7,901,436 B2 * | 3/2011 | Baccelli .................. 606/272 |
| 2003/0023243 A1 | 1/2003 | Biedermann et al. |
| 2003/0045874 A1 * | 3/2003 | Thomas, Jr. ................ 606/61 |
| 2004/0143265 A1 | 7/2004 | Landry et al. |
| 2004/0172022 A1 | 9/2004 | Landry et al. |
| 2005/0149019 A1 * | 7/2005 | Sasing et al. ................ 606/61 |
| 2007/0016189 A1 * | 1/2007 | Lake et al. ................. 606/61 |
| 2007/0083199 A1 * | 4/2007 | Baccelli .................... 606/61 |

FOREIGN PATENT DOCUMENTS

| | | |
|---|---|---|
| FR | 2795622 A1 | 1/2001 |
| WO | WO02/15766 A2 | 2/2002 |

OTHER PUBLICATIONS

Lenke, Lawrence G., "Segmental Spinal Stabilization Using a Low-Profile Crosslinking Device," retrieved Jan. 25, 2010 from http://www.spineuniverse,com/exams-tests/devices/segmental-spinal-stabilization-using-low-profile; posted Feb. 13, 2004, 3 pages.

* cited by examiner

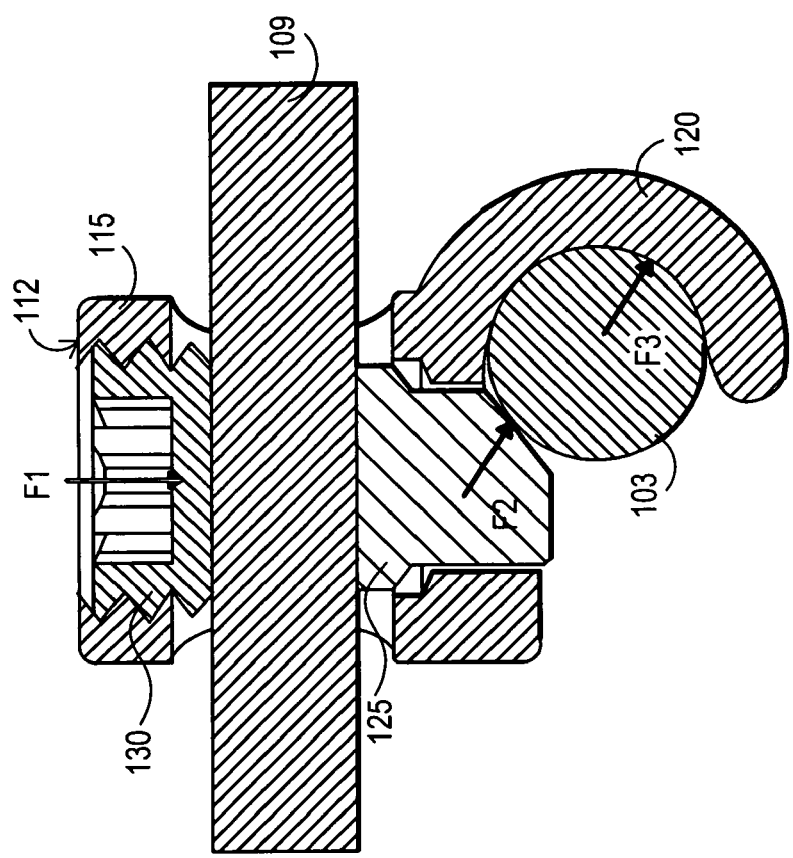

APPARATUS AND METHODS FOR SPINAL IMPLANT WITH VARIABLE LINK MECHANISM

TECHNICAL FIELD

The inventive concepts relate generally to spinal implants. More particularly, the invention concerns apparatus and associated methods for articulating variable cross-link or transverse connectors or devices for use in spinal implants.

BACKGROUND

Modern spine surgery often involves the use of spinal implants to correct or treat various spine disorders or to support the spine. Spinal implants may help, for example, to stabilize the spine, correct deformities of the spine, facilitate fusion, or treat spinal fractures. Typical spinal implants may include rigid (i.e., in a fusion procedure) support for the affected regions of the spine. They either limit movement in the affected regions in virtually all directions (for example, in a fused region).

Fusion or rigid implants typically use longitudinal rods to support parts of the spine. The rods usually do not provide much protection against torsional forces or movement. To address that concern, cross-link devices have been used. The conventional cross-link devices, however, suffer from disadvantages, such as limited range of motion (to allow the surgeon to adjust the implant to the patient's needs and anatomy), a relatively large number of fasteners to adjust, etc. A need exists for a variable cross-link or transverse connector that addresses those deficiencies.

SUMMARY

The inventive concepts relate to apparatus and methods for spinal implants with variable cross-link devices or poly-axial connectors. In one exemplary embodiment, an implant includes a locking mechanism. The locking mechanism includes a rod engaging member. The rod engaging member is configured to facilitate a compression fit to two implant rods. The implant rods may constitute two longitudinal rods, or a longitudinal rod and a transverse rod, as desired.

In another exemplary embodiment, a system for supporting a spine includes two longitudinal rods, and a transverse rod. The system further includes at least one variable cross-link device, having a body. The variable cross-link device is configured to simultaneously couple the transverse rod to a respective one of the longitudinal rods when a plug is engaged with the body of that variable cross-link device.

Yet another exemplary embodiment concerns a method of coupling a pair of longitudinal rods in a spinal implant by using a transverse rod and a pair of poly-axial connectors. The method includes tightening a fastener in one of the poly-axial connectors in order to couple that connector to one of the longitudinal rods and to the transverse rod. The method further includes tightening a fastener in the other poly-axial connector in order to couple that connector to the other longitudinal rod and to the transverse rod.

BRIEF DESCRIPTION OF THE DRAWINGS

The appended drawings illustrate only exemplary embodiments of the invention and therefore should not be considered or construed as limiting its scope. Persons of ordinary skill in the art who have the benefit of the description of the invention appreciate that the disclosed inventive concepts lend themselves to other equally effective embodiments. Unless noted otherwise, in the drawings, the same numeral designators used in more than one drawing denote the same, similar, or equivalent functionality, components, or blocks.

FIG. 8 illustrates a cross-section of the variable cross-link device shown in FIG. 4.

DETAILED DESCRIPTION

The disclosed novel concepts relate to spinal implants with variable cross-link devices or transverse connectors. The cross-link devices provide poly-axial or variable motion, thus providing several degrees of freedom and facilitating conforming the implant to the patient's anatomy or desired formation or structure.

The cross-link devices allow supporting of the spine in fusion procedures. More specifically, the cross-link devices help to limit or eliminate undesired motion (e.g., torsional movement) in a fusion implant. In other applications, the variable cross-link devices help the surgeon to extend a fused portion of the spine to additional levels. In such cases, the surgeon may use extended longitudinal rods, and use cross-link devices to provide additional support and to link the new implants to the existing implants. The novel cross-link devices provide several advantages over conventional devices, as persons of ordinary skill in the art who have the benefit of the description of the invention appreciate.

Figure 1:
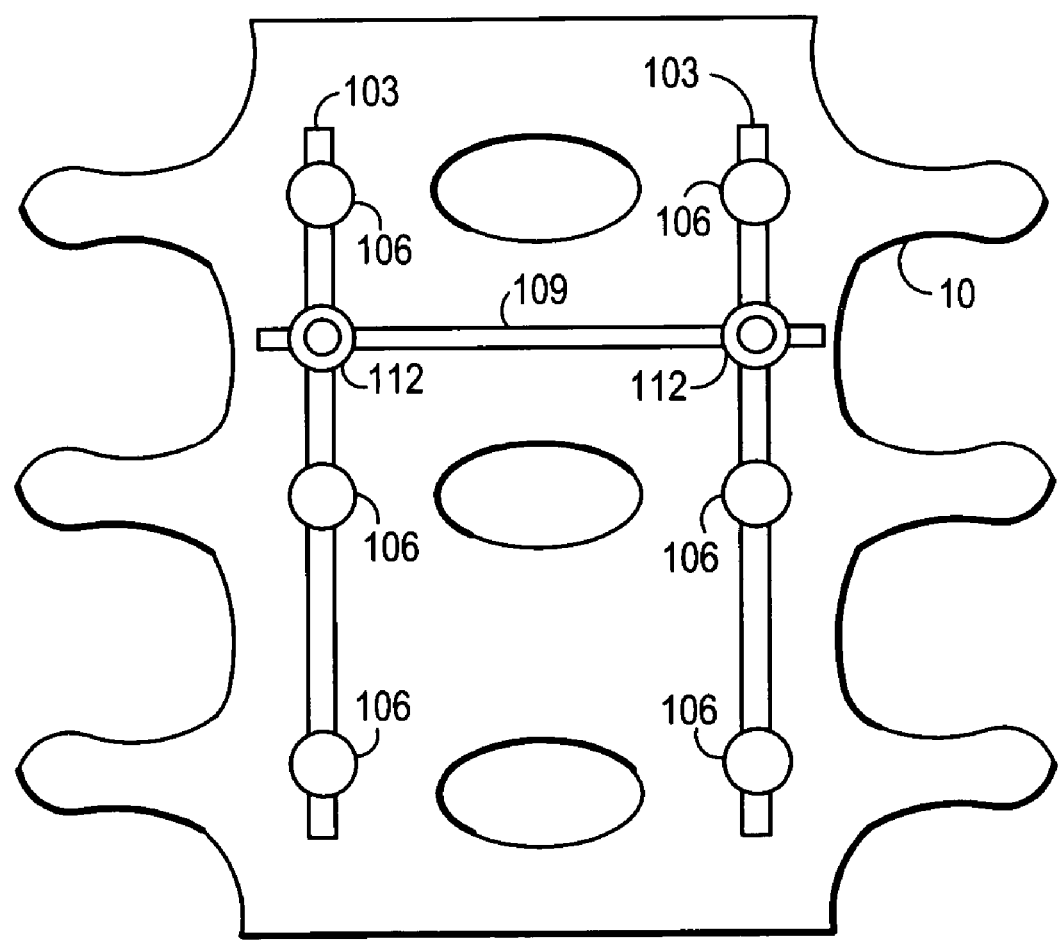
FIG. 1 shows a spinal implant system that includes a variable cross-link device or transverse connector according to an illustrative embodiment of the invention.

FIG. 1 shows a spinal implant system that includes a variable cross-link device or transverse connector according to an illustrative embodiment of the invention. The implant system may include a pair of longitudinal rods or elongated members 103. Longitudinal rods 103 are affixed to spine 10 of the patient, disposed generally in a vertical direction along spine 10.

The surgeon may use a variety of techniques to affix longitudinal rods 103 to spine 10, as desired, and as persons of ordinary skill in the art who have the benefit of the description of the invention understand. For example, the surgeon may use coupling elements 106, which may include fasteners such as screws, caps, set screws, hooks, etc. In one embodiment, coupling elements 106 may include pedicle screws, as persons of ordinary skill in the art who have the benefit of the description of the invention understand.

The longitudinal rods 103 immobilize and support one or more levels of spine 10. More specifically, during a surgical procedure, the surgeon uses coupling elements 106 to affix longitudinal rods 103 to the vertebrae of spine 10. Longitudinal rods 103 support and/or immobilize spine 10 and facilitate fusion in one or more levels, as desired, depending on the nature of the defect or injury in spine 10. Persons of ordinary skill in the art who have the benefit of the description of the invention understand the details of the procedures, as well as the instruments and devices used to affix longitudinal rods 103 to spine 10.

The spinal implant system also includes a plurality of cross-link devices 112 (or poly-axial connectors), and one or more transverse rods or elongated members 109. Each pair of cross-link devices 112 couples to longitudinal rods 103 and also to a respective transverse rod 109.

By using variable cross-link devices 112, the surgeon may also couple longitudinal rods 103 to each other at one or more locations, as desired. More specifically, at one or more desired locations, the surgeon may use a pair of variable cross-link devices 112 (or poly-axial connectors), together with transverse rod 109, to further support and immobilize the spine.

Put another way, variable cross-links 112, when used with transverse rod 109, provide additional rigidity to the spinal implant. The additional rigidity helps to reduce, limit, or eliminate undesired motions or stresses. For example, the implant tends to limit or eliminate torsional movements in the affected levels of spine 10, provides torsional stability to spine 10, and therefore facilitates fusion in one or more desired levels.

Compared to conventional approaches, variable cross-link devices according to the invention offer several advantages. In a typical implant procedure, the surgeon forms longitudinal rods 103 to conform them to the patient's anatomy, i.e., the physical properties and geometry of spine 10. With conventional approaches, the surgeon also forms longitudinal rods 103 in order to conform them to the cross-link device.

As described below in detail, variable cross-link devices 112 according to the invention provide the surgeon with more flexibility, and help achieve a better fit among the various parts of the implant. Viewed another way, by providing variable transverse cross-linking or coupling between longitudinal rods 103, cross-link devices 112 more readily conform to the geometry and shape of longitudinal rods 103 and the anatomy of spine 10.

Accordingly, the surgeon need not contour the cross-link devices and/or the rods in order to fit an implant to a particular patient's anatomy. By conforming to the patient's anatomy, spinal implant systems according to the invention provide better support and immobilization of spine 10, thus accelerating the healing or fusion process.

Furthermore, conventional approaches often involve positioning and fastening a relatively large number of fasteners in order to situate the cross-link devices as part of the implant. As described below in detail, the variable cross-link devices according to the invention, however, use a novel approach of transmitting force from a relatively small number of fasteners in order to couple to longitudinal rods 103 and transverse rod 109.

Figure 2:
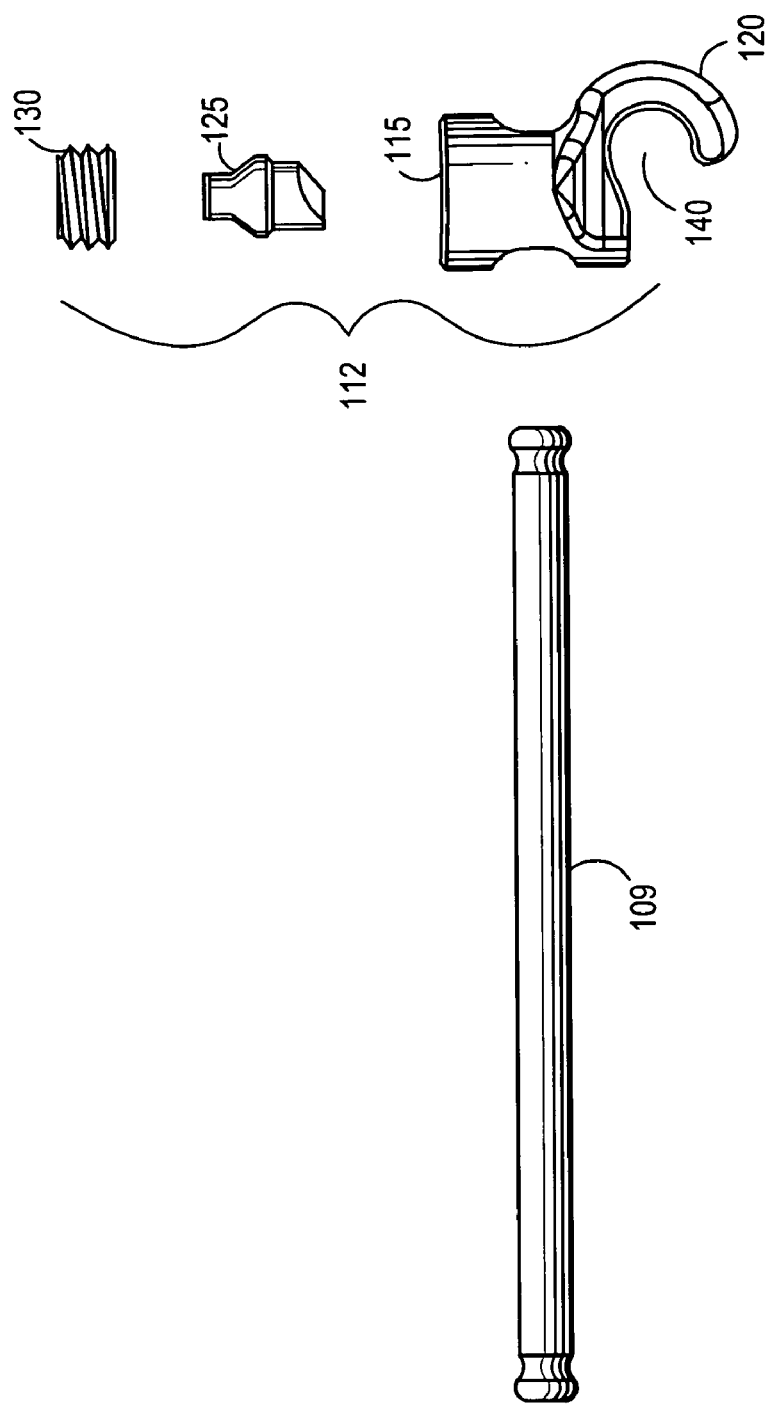
FIG. 2 illustrates an exploded view of variable cross-link devices according to an illustrative embodiment of the invention.

FIG. 2 shows an exploded view of variable cross-link devices 112 according to an illustrative embodiment of the invention. The following description discusses variable cross-link device 112 on the right side of the figure; a similar description applies to the cross-link device on the left side of the figure.

Variable cross-link device 112 includes body 115, piston or rod engaging member 125, and screw or closure top or cap or plug 130. Note that, in one embodiment, cross-link device 112 may also include transverse rod 109, as desired. In other words, the cross-link device may comprise either a connector (body 115, rod engaging member 125, and plug 130), or a combination of a connector with a transverse rod 109 (e.g., as an integral unit). In another embodiment, one may provide the variable cross-link as a combination of two variable cross-link devices 112 pre-assembled with a transverse rod 109, as desired.

Body 115 has an opening or through hole (not shown explicitly) that allows an end of transverse rod 109 to pass through body 115. The end of transverse rod 109 may protrude from body 115, as shown more clearly in FIG. 2.

The hole may have a diameter larger than the diameter of transverse rod 109, as desired. That arrangement allows positioning transverse rod 109 in a number of positions with respect to body 115 of variable cross-link device 112. Thus, when affixing the implant in spine 10, the surgeon may rotate body 115 with respect to transverse rod 109 in order to fit the implant to the patient's anatomy, or fit variable cross-link device 112 to the shape and structure of longitudinal rod(s) 103 and transverse rod 109.

Referring back to FIG. 2, body 115 includes a curved or hook element or member 120. Curved member 120 outlines an opening or recess 140. Opening 140 engages with longitudinal rod 103 (not shown explicitly), and helps couple body 115 to longitudinal rod 103. Body 115 may be made of a desired suitable material, such as titanium.

Body 115 receives piston or rod engaging member 125. Rod engaging member 125 couples to transverse rod 109, and couples body 115 to transverse rod 109. As described below in detail, rod engaging member 125 also couples curved member 120 to longitudinal rod 103 (not shown explicitly).

In the embodiment shown, rod engaging member 125 has a "U"-shaped portion or slot for engaging or coupling to one end of transverse rod 109. The exemplary embodiment of rod engaging member 125 in FIG. 2 also has a beveled portion or face, or conical face, that engages with, or couples to, longitudinal rod 103 (not shown explicitly). Rod engaging member 125 may be made of a variety of suitable materials, for example, titanium.

Plug 130 screws or fastens in the top part of body 115. Plug 130 may have a variety of shapes, for example, it may have a hexagonal head. Plug 130 may be made of a desired suitable material, such as titanium.

When fastened in body 115, plug 130 couples to transverse rod 109, and exerts force onto it. Transverse rod 109 transmits or transfers this force to rod engaging member 125. In response, rod engaging member 125 provides a compression coupling or fit to transverse rod 109. Advantageously, rod engaging member 125 also provides a compression coupling or fit to longitudinal rod 103 (not shown explicitly).

Note that the implant may include mechanisms to prevent or reduce the possibility of loosening or dislodging, either during surgery or thereafter, as desired. For example, the end(s) of transverse rod 109 may be widened to prevent it from uncoupling from device(s) 112, by expanding the end(s) of rod 109 by applying force to it and deforming it (e.g., shaping or turning it to a ball or round shape). As another example, a "stake" may be added to plug 130 to prevent it from loosening or falling out.

Figure 3:
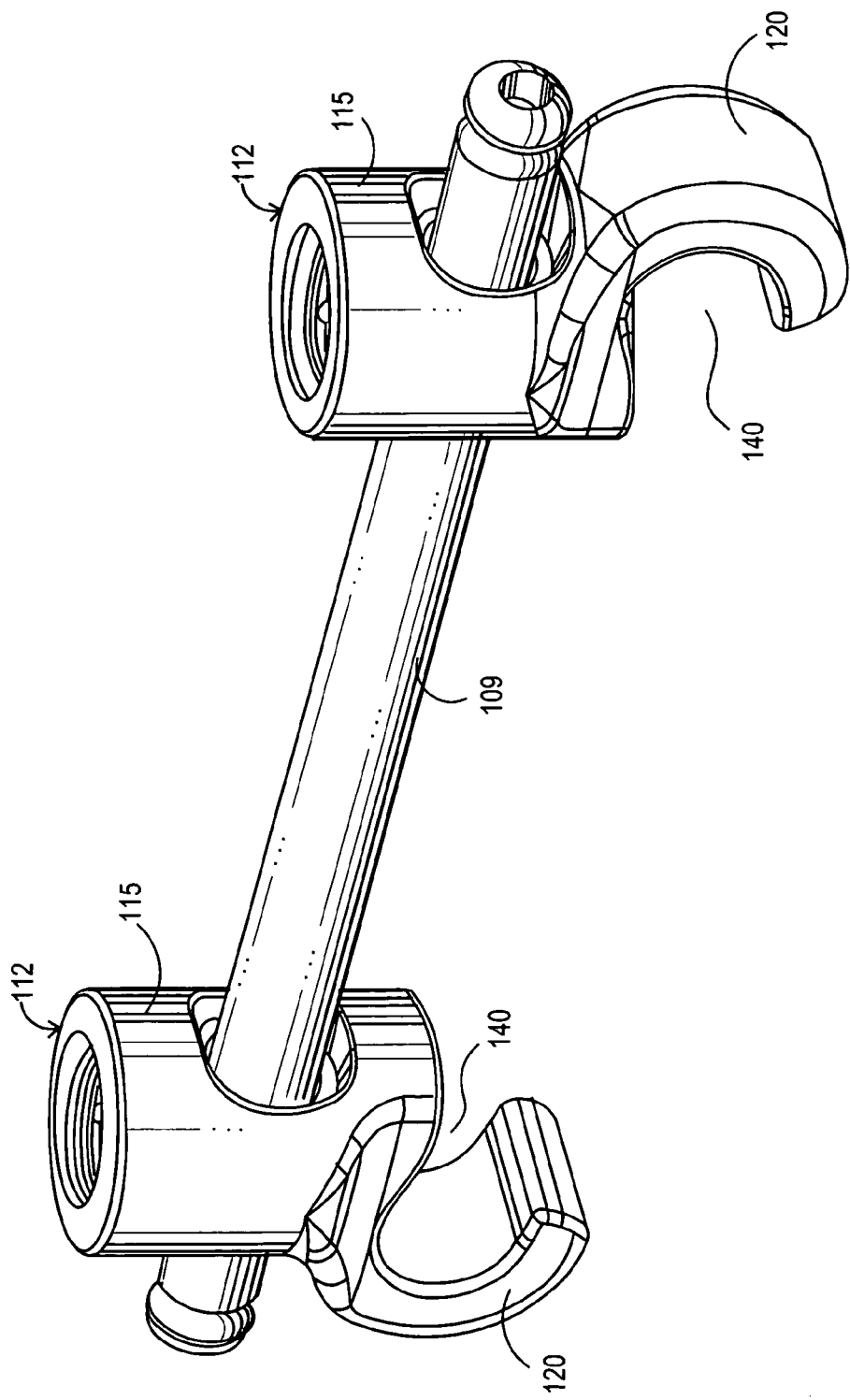
FIG. 3 depicts a perspective view of variable cross-link devices according to an exemplary embodiment of the invention.

FIG. 3 depicts a perspective view of a pair of variable cross-link devices according to an exemplary embodiment of the invention. More particularly, the illustration shows a pair of cross-link devices 112 coupled to a transverse rod 109.

Note that, as noted above, in the embodiment shown, body 115 of variable cross-link device 112 includes an elongated, elliptical, or oblong hole. The topology of the hole allows rotation of body 115 with respect to transverse rod 109, thus providing the surgeon with an additional degree of freedom.

Furthermore, as noted above, body 115 includes curved member or hook 120, shaped for coupling to longitudinal rod 103 (not shown explicitly). The inside surface of curved member 120 may be shaped in order to couple to longitudinal rod 103, and provide a compression or friction fit to it.

The surgeon may position each of variable cross-link devices 112 in a desired position along transverse rod 109. More specifically, the surgeon may slide each of variable cross-link devices 112 along transverse rod 109 and fasten it in a position that accommodates the anatomy of spine 10, the position and shape of longitudinal rods 103, or both, as desired. In this manner, the inventive variable cross-link devices provide the surgeon with a degree of freedom in positioning and securing the implant within the patient's body.

Figure 4:
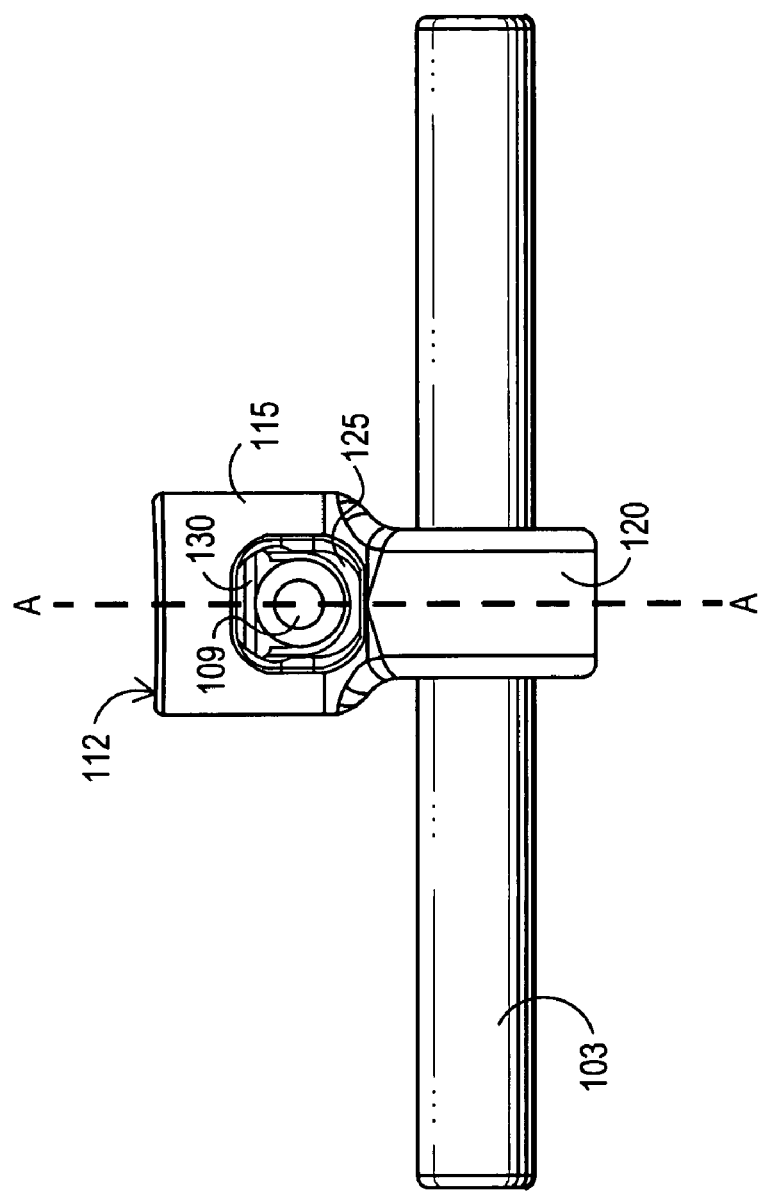
FIG. 4 shows a side view of a variable cross-link device according to an exemplary embodiment of the invention.

FIG. 4 shows a side view of a variable cross-link device 112 according to an exemplary embodiment of the invention. More specifically, the figure shows how curved member 120 of body 115 of the variable cross-link device 112 couples to longitudinal rod 103. Put another way, curved member 120 of body 115 "wraps" at least part-way around longitudinal rod 103, and provides a compression or friction fit to it (in response to the force exerted by fastening plug 130, as described below in detail).

As shown in the figure, rod engaging member 125 has a channeled or "U"-shaped slot that engages transverse rod 109. The pressure exerted from fastening plug 130 compresses or presses transverse rod 109 against rod engaging member 125. The "U"-shaped slot of rod engaging member 125 may match the physical characteristics of transverse rod 109, and thus facilitate a compression or friction fit to it.

For example, the width of the opening in the "U"-shaped slot of rod engaging member 125 may be close to, or the same as, the diameter of transverse rod 109. This arrangement would result in a relatively tight compression or friction fit between rod engaging member 125 and transverse rod 109. From a broader perspective, the compression or friction fit provides a relatively tight coupling of plug 130, rod engaging member 125, transverse rod 109, and body 115 to one another.

Figure 5:
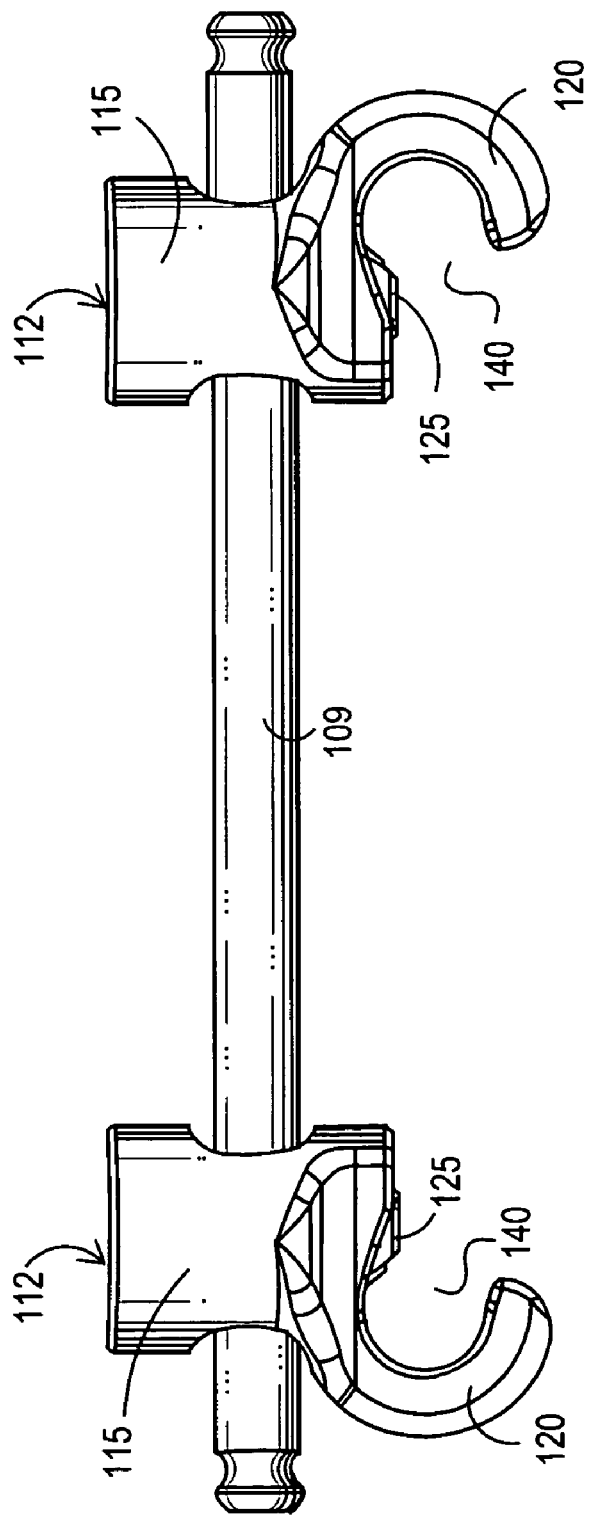
FIG. 5 illustrates an end view of variable cross-link devices according to an exemplary embodiment of the invention.

FIG. 5 illustrates an end view of a pair of variable cross-link devices 112 according to an exemplary embodiment of the invention, coupled to a transverse rod 109. Note that the shape of curved member or hook 120 allows "wrapping" around a longitudinal rod 103 (not shown explicitly), as described above. Put another way, curved member 120 receives or wraps around (at least partially) the lateral outside surface of the longitudinal rod 103 to which it couples.

Furthermore, note that rod engaging member 125 in each variable cross-link device 112 protrudes from body 115. The protruding portion of rod engaging member 125 helps to provide a compression or friction fit to longitudinal rod 103.

The inventive variable cross-link devices 112 provide flexibility to the surgeon in shaping an implant system that suits the needs or anatomy of a particular patient. In an implant system using variable cross-link devices 112, longitudinal rods 103 may be parallel or non-parallel to each other, as desired. Furthermore, longitudinal rods 103 may be skewed in orientation with respect to each other. Thus, longitudinal rods 103 may be diverging or converging with respect to each other, as desired.

Figure 6:
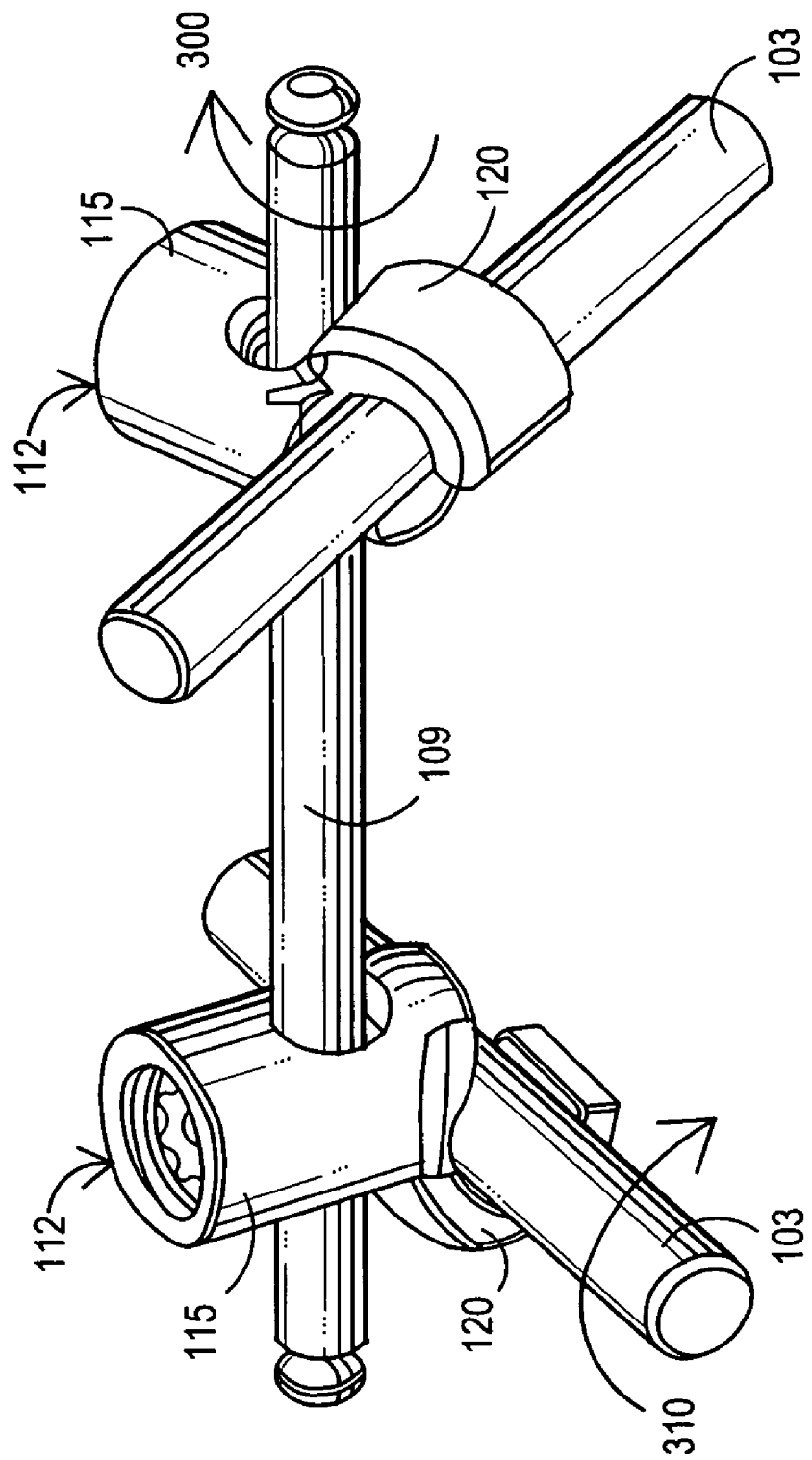
FIG. 6 depicts a transverse connection using variable cross-link devices according to an exemplary embodiment of the invention.

FIG. 6 depicts a transverse connection of longitudinal rods 103, using variable cross-link devices 112 according to an exemplary embodiment of the invention. In this configuration, a pair of variable cross-link devices 112 couple to each other a pair of vertically skewed longitudinal rods 103. In other words, longitudinal rods 103 do not occupy the same plane along spine 10.

Because of the flexibility that variable cross-link devices 112 provide, the surgeon may rotate or skew longitudinal rods 103 with respect to each other, as desired. Thus, the surgeon may rotate each variable cross-link device 112 with respect to transverse rod 109, and thus accommodate a vertically skewed implant, as desired.

Figure 7:
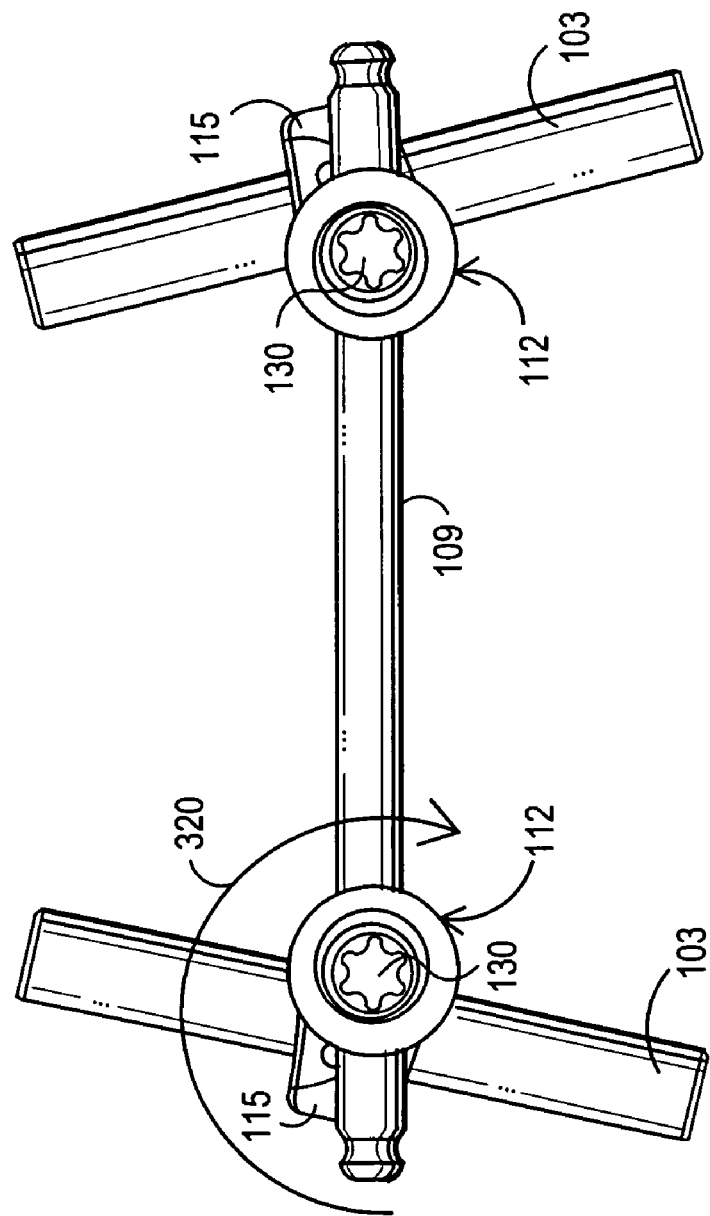
FIG. 7 shows another transverse connection using variable cross-link devices according to an exemplary embodiment of the invention.

FIG. 7 shows another transverse connection of longitudinal rods 103, using variable cross-link devices 112 according to an exemplary embodiment of the invention. In this arrangement, a pair of variable cross-link devices 112 couple to each other a pair of horizontally skewed longitudinal rods 103.

Put another way, longitudinal rods 103 may occupy the same horizontal plane (e.g., a plane along spine 10). They, however, may have a non-parallel configuration and diverge from each other or converge towards each other. As an example, the surgeon may wish to design converging longitudinal rods 103 in order to accommodate a progressively narrower spine.

Variable cross-link devices 112 provide the surgeon with additional flexibility by allowing the surgeon to skew longitudinal rods 103 with respect to each other, in either a converging or diverging configuration, as desired. The choice of the arrangement depends on factors such as the patient's anatomy, the size and configuration of the components, etc., as persons of ordinary skill in the art who have the benefit of the description of the invention understand.

Generally speaking, the variable cross-link devices (or poly-axial connectors) according to the invention provide five degrees of freedom or variations of movement. The variations of movement may occur in two axes (i.e., the x, and y axes), and movement about three axes (i.e., movement or rotation about each of the x, y, and z axes, 300, 310, 320) as shown in FIGS. 6 and 7.

The cross-link provides the capability for horizontal adjustment along the length of transverse rod 109, vertical adjustment along longitudinal rods 103, and anterior/posterior adjustment on longitudinal rods 103. Thus, the variable cross-link devices allow locking transverse rod 109 and longitudinal rods 103 without limiting their freedoms of movement (or variations of movement).

Variable cross-link devices according to the invention provide the additional advantage that, by fastening plug 130, the surgeon can couple a variable cross-link device 112 to both longitudinal rod 103 and transverse rod 109. (Note that, to lock the variable cross-link device at the other end of transverse rod 109, the surgeon may use a similar procedure.) Locking variable cross-link device 112 to longitudinal rod(s) 103 and transverse rod 109 prevents or limits further movement or articulation of the implant.

Rather than fastening multiple fasteners, as is the case with conventional cross-link devices, the surgeon fastens plug 130 for each variable cross-link device 112. This feature simplifies the operation, reduces the number of steps that the surgeon takes, and may reduce the number of physical components.

FIG. 8 illustrates a cross-section of variable cross-link device 112 shown in FIG. 4. More specifically, FIG. 8 shows a cross-section along the line marked A-A in FIG. 4 of variable cross-link device 112. The cross-section shown in FIG. 8 illustrates the details of how the surgeon may affix variable cross-link device 112 by fastening plug 130.

To fasten variable cross-link device 112 to both longitudinal rod 103 and transverse rod 109, the surgeon fastens plug 130. Fastening plug 130 exerts a force (labeled "F1" in FIG.

8) to transverse rod 109, and provides a compression fit between body 115, plug 130, and rod engaging member 125 of variable cross-link device 112 and transverse rod 109.

Fastening plug 130 also pushes transverse rod 109 against rod engaging member 125. Thus, plug 130 causes rod engaging member 125 to extend downward into body 115 of variable cross-link device 112.

The extension of rod engaging member 125 in body 115 causes the beveled portion of rod engaging member 125 to contact longitudinal rod 103, and exert a force (labeled "F2" in FIG. 8) against it. The application of this force helps to provide a compression or friction fit between rod engaging member 125 and longitudinal rod 103.

The application of force against longitudinal rod 103 causes it to exert a force (labeled "F3") against curved member 120 of body 115 of variable cross-link device 112. The exertion of force against curved member 120 further causes a compression or friction fit between it and longitudinal rod 103.

Thus, by fastening plug 130, the surgeon can simultaneously cause a compression or friction fit between variable cross-link device 112 and both transverse rod 109 and longitudinal rod 103. Accordingly, unlike conventional devices, the surgeon need not fasten separate or individual fasteners.

Note that, rather than coupling a longitudinal rod 103 to a transverse rod 109, one may use the poly-axial connectors according to the invention to couple two longitudinal rods 103, as desired. In such an embodiment, the slot in body 115 for accommodating transverse rod 109 may be parallel to longitudinal rod 103 (or a desired angle with respect to rod 103), rather than being normal (or substantially or nearly normal) to longitudinal rod 103. Such a configuration allows coupling two rods 103, or two sections or pieces of rods 103, to be coupled together, including the advantages of the connectors according to the invention, as described herein.

The implants according to the invention, including the variable cross-link devices (or poly-axial connectors) may be used in minimally invasive surgery (MIS) procedures or in non-MIS procedures, as desired, and as persons of ordinary skill in the art who have the benefit of the description of the invention understand. MIS procedures seek to reduce cutting, bleeding, and tissue damage or disturbance associated with implanting a spinal implant in a patient's body. Exemplary procedures may use a percutaneous technique for implanting longitudinal rods and coupling elements. Examples of MIS procedures and related apparatus are provided in U.S. patent application Ser. No. 10/698,049, filed Oct. 30, 2003, U.S. patent application Ser. No. 10/698,010, Oct. 30, 2003, and U.S. patent application Ser. No. 10/697,793, filed Oct. 30, 2003, incorporated herein by reference.

The variable cross-link devices (or poly-axial connectors) according to the invention are suitable for use with MIS procedures because plug 130 (used to lock the rods) is tightened or fastened to the longitudinal rods from above. In such an MIS procedure, the surgeon may percutaneously position and place the implant using the same technique and through the same wound exposure as with other spinal implants, then tighten or fasten plug 130 by inserting. Because plug 130 is accessible through the wound, one may couple the rods together by tightening plug 130, as described above in detail, without using additional incisions or wounds.

Implanting the variable cross-link devices (or poly-axial connectors) does not entail additional exposures or cuts, as all insertion and locking of the poly-axial connector may be performed through the two existing exposure sites used to implant the longitudinal rods. Other details of the procedure will be apparent to persons of ordinary skill in the art who have the benefit of the description of the invention.

Various modifications and alternative embodiments of the invention in addition to those described here will be apparent to persons of ordinary skill in the art who have the benefit of the description of the invention. Accordingly, the manner of carrying out the invention as shown and described are to be construed as illustrative only.

Persons skilled in the art may make various changes in the shape, size, number, and/or arrangement of parts without departing from the scope of the invention described in this document. For example, persons skilled in the art may substitute equivalent elements for the elements illustrated and described here, or use certain features of the invention independently of the use of other features, without departing from the scope of the invention.

The invention claimed is:

1. A system for supporting a spine, comprising:
   a longitudinal rod disposed generally in a first direction along a spine;
   a transverse rod disposed generally in a second direction transverse to the spine; and
   a variable cross-link device, wherein the variable cross-link device comprises a body, a plug, and a rod engaging member,
      wherein the rod engaging member comprises a U-shaped portion at a first end and an angled surface at a second end,
      wherein the body comprises openings to receive a portion of the transverse rod, a generally c-shaped hook to couple to a portion of the longitudinal rod, and a channel along a central axis of the body to receive the plug and the rod engaging member,
      wherein the angled surface of the rod engaging member is shaped for contact with the longitudinal rod coupled to the generally c-shaped hook of the body,
      wherein the U-shaped portion of the rod engaging member is shaped to engage with the transverse rod in the channel of the body, and
      wherein the longitudinal rod and the transverse rod are held in rigid connection relative to one another by friction fit when the plug screws into the body to exert a force directly onto the transverse rod, said transverse rod transferring the force directly to the rod engaging member, wherein advancement of said rod engaging member forces the longitudinal rod against an interior curved surface of the generally c-shaped hook to provide compression fit of the generally c-shaped hook to the longitudinal rod.

2. The system aim 1, further comprising a second longitudinal rod and a second variable cross-link device for connecting the transverse rod with the second longitudinal rod.

3. The system of claim 1, wherein the body comprises a hole, said hole configured to receive the transverse rod, and wherein the hole has a diameter larger than a diameter of the transverse rod to allow the transverse rod be angled relative to the longitudinal rod about the axis in which the plug is screwed into the body.

4. The system of claim 1, wherein the U-shaped portion of the rod engaging member comprises a slot configured to couple to the transverse rod.

5. The system of claim 1, further comprising a pedicle screw, wherein the pedicle screw is configured to secure the longitudinal rod to a vertebra of the spine.

6. The system of claim 1, wherein the transverse rod consists of a unitary piece of metal.

7. The system of claim 1, wherein the openings of the body comprise a hole that is shaped to receive the transverse rod.

8. The system of claim 1, wherein the system comprises titanium.

9. A variable cross-link device, comprising:
   a body having a channel along a central axis of the body;
   a plug; and
   a rod engaging member having a U-shaped portion at a first end and an angled surface at a second end,
   wherein the channel of the body is shaped to receive the rod engaging member and the plug,
   wherein the body further comprises a first opening for receiving a first rod between the plug and the rod engaging member and a generally c-shaped hook for receiving a second rod, wherein the first rod is a transverse rod disposed generally in a first direction along a spine, wherein the second rod is a longitudinal rod disposed generally in a second direction transverse to the spine, wherein when the rod engaging member is inserted in the channel of the body, the transverse rod engages with the U-shaped portion of the rod engaging member through the first opening of the body and the longitudinal rod engages with the generally c-shaped hook of the body and with the rod engaging member protruding from the body through the channel of the body, wherein advancement of the rod engaging member forces the longitudinal rod against an interior curved surface of the generally c-shaped hook to provide compression fit of the generally c-shaped hook to the longitudinal rod.

10. A method for stabilizing a portion of a spine, comprising:
    coupling a longitudinal rod to a first side of the portion of the spine generally in a first direction along the portion of the spine using at least two fasteners;
    positioning a cross-linking device on the longitudinal rod between the two fasteners, wherein the cross-linking device comprises:
      a body having a generally c-shaped hook for receiving the longitudinal rod between the two fasteners and a channel along a central axis of the body;
      a plug; and
      a rod engaging member having a U-shaped portion at a first end and an angled surface at a second end, wherein the channel of the body is shaped to receive the rod engaging member and the plug;
    positioning the rod engaging member in the channel so the angled surface of the rod engaging member contacts the longitudinal rod received by the generally c-shaped hook:
    positioning, generally in a second direction transverse to the portion of the spine, a transverse rod through an opening of the body to engage with the U-shaped portion of the rod engaging member positioned in the channel of the body;
    advancing the plug in the channel of the body to contact the transverse rod, wherein the transverse rod engages the rod engaging member, wherein the rod engaging member engages the longitudinal rod via the angled surface of the rod engaging member protruding from the body, wherein advancement of said rod engaging member forces the longitudinal rod against an interior surface of the generally c-shaped hook to provide a compression fit of the generally c-shaped hook of the body to the longitudinal rod; and
    securing the plug onto the body.

\* \* \* \* \*

UNITED STATES PATENT AND TRADEMARK OFFICE
CERTIFICATE OF CORRECTION

| | | |
|---|---|---|
| PATENT NO. | : 8,226,689 B2 | Page 1 of 1 |
| APPLICATION NO. | : 11/234706 | |
| DATED | : July 24, 2012 | |
| INVENTOR(S) | : Robert J. Jones et al. | |

It is certified that error appears in the above-identified patent and that said Letters Patent is hereby corrected as shown below:

Column 8
Line 51, delete "aim", and insert therefore -- of claim --.

Signed and Sealed this
Twenty-fifth Day of September, 2012

David J. Kappos
*Director of the United States Patent and Trademark Office*